US008236495B2

(12) United States Patent
Nochumson et al.

(10) Patent No.: US 8,236,495 B2
(45) Date of Patent: *Aug. 7, 2012

(54) PROCESS AND EQUIPMENT FOR PLASMID PURIFICATION

(76) Inventors: Samuel Nochumson, The Woodlands, TX (US); Ross Durland, The Woodlands, TX (US); Audrey Yu-Speight, Austin, TX (US); John Welp, Willis, TX (US); Kuowei Wu, Houston, TX (US); Rexford Hayes, Milford, MA (US)

(*) Notice: Subject to any disclaimer, the term of this patent is extended or adjusted under 35 U.S.C. 154(b) by 1523 days.

This patent is subject to a terminal disclaimer.

(21) Appl. No.: 11/327,987

(22) Filed: Jan. 9, 2006

(65) Prior Publication Data

US 2006/0106208 A1 May 18, 2006

Related U.S. Application Data

(63) Continuation of application No. 09/774,284, filed on Jan. 29, 2001, now Pat. No. 7,026,468, which is a continuation of application No. 08/887,673, filed on Jul. 3, 1997, now abandoned.

(51) Int. Cl.
*C12Q 1/68* (2006.01)
*C02F 1/02* (2006.01)
*B01D 15/00* (2006.01)

(52) U.S. Cl. ............................ 435/6.1; 210/600; 210/660

(58) Field of Classification Search .................. None
See application file for complete search history.

(56) References Cited

U.S. PATENT DOCUMENTS

| | | |
|---|---|---|
| 3,928,642 A | 12/1975 | Hubert et al. |
| 4,314,974 A | 2/1982 | Libby et al. |
| 4,450,103 A | 5/1984 | Konrad et al. |
| 4,462,940 A | 7/1984 | Hanisch et al. |
| 4,621,061 A | 11/1986 | Puehler et al. |
| 4,623,723 A | 11/1986 | Keller et al. |
| 4,780,210 A | 10/1988 | Hsia |
| 4,830,969 A | 5/1989 | Holmes |
| 4,900,677 A | 2/1990 | Hewitt |
| 4,985,552 A | 1/1991 | Fedeli et al. |
| 4,997,932 A | 3/1991 | Reardon et al. |
| 5,034,314 A | 7/1991 | Geiger et al. |
| 5,057,426 A | 10/1991 | Henco et al. |
| 5,096,818 A | 3/1992 | DeBonville |
| 5,208,160 A | 5/1993 | Kikyotani et al. |
| 5,256,294 A | 10/1993 | van Reis |
| 5,300,433 A | 4/1994 | Hrinda et al. |
| 5,561,064 A * | 10/1996 | Marquet et al. ............ 435/320.1 |
| 5,707,812 A | 1/1998 | Horn et al. |
| 5,792,651 A | 8/1998 | Colpan et al. |
| 5,837,529 A | 11/1998 | Wan et al. |
| 5,981,735 A * | 11/1999 | Thatcher et al. ............ 536/25.4 |
| 5,990,301 A | 11/1999 | Colpan et al. |
| 6,011,148 A | 1/2000 | Bussey et al. |
| 6,197,553 B1 | 3/2001 | Lee et al. |
| 6,214,586 B1 | 4/2001 | McNeilly |
| 6,277,648 B1 | 8/2001 | Colpan |
| 6,297,371 B1 | 10/2001 | Colpan et al. |
| 6,750,333 B1 | 6/2004 | Kuhne |
| 2002/0198372 A1 | 12/2002 | Bridenbaugh et al. |

FOREIGN PATENT DOCUMENTS

| | | |
|---|---|---|
| AU | 723817 | 3/1998 |
| EP | 0 240 191 | 10/1987 |
| EP | 0 376 080 | 7/1990 |
| EP | 0 431 905 | 6/1991 |
| EP | 0 517 515 A2 | 6/1992 |
| EP | 0 814 156 A2 | 6/1997 |
| JP | 58013519 | 1/1983 |
| JP | A 58013519 | 1/1983 |
| WO | WO 87/07645 | 12/1986 |
| WO | WO 89/01035 | 2/1989 |
| WO | WO 95/21177 | 8/1995 |
| WO | WO 95/21250 | 8/1995 |
| WO | WO 96/02658 A1 | 2/1996 |
| WO | WO 96/08500 | 3/1996 |
| WO | WO 96/21729 | 7/1996 |
| WO | WO 97/23601 | 7/1997 |
| WO | WO 97/35002 | 9/1997 |
| WO | WO 98/01540 | 1/1998 |
| WO | WO 98/11208 | 3/1998 |
| WO | WO 99/63076 | 12/1999 |

OTHER PUBLICATIONS

Morris et al., "Purification and separation of holo- and apo-forms of *Saccharopolyspora erythraea* acyl-carrier protein released from recombinant *Escherichia coli* by freezing and thawing," Biochem. J., 1993, vol. 294, pp. 521-527.*
Colote et al., "Analysis and Purification of Plasmid DNA by Reverse-Phase High-Performance Liquid Chromatography," Analytical Biochemistry, 1986, vol. 154, pp. 15-20.*
Amersham Biosciences. *Hydrophobic Interaction Chromatography: Principles and Methods.* Amersham Pharmacia Biotech AB Edition: Uppsala, Sweden (2000).
Birnboim et al. "A Rapid Alkaline Extraction Procedure for Screening Recombinant Plasmid DNA." *Nucleic Acids Research* 7 (1979) 1513-23.
Carlson et al. "Mechanical Disruption of *Escherichia coli* for Plasmid Recovery." *Biotechnology and Bioengineering* 48 (1995) 303-15.
Chandra, G. et al. "Large-Scale Purification of Plasmid DNA by Fast Protein Liquid Chromatography Using a Hi-Load Q Sepharose Column." *Analytical Biochemistry* 203 (1992) 169-72.
Coppella, S. et. al. "Isolation of High-Molecular-Weight Nucleic Acids for Copy Number Analysis Using High-Performance Liquid Chromatography." *Journal of Chromatography* 402 (1987) 189-99.
Davis. "Comparison of Plasmid DNA Preparation Methods for Direct Gene Transfer and Genetic Immunization "*BioTechniques* 21 (Jul. 1996) 92-9.

(Continued)

*Primary Examiner* — Young J Kim
(74) *Attorney, Agent, or Firm* — D. Benjamin Berson; Ph. D., Borson Law Group, PC

(57) ABSTRACT

A scalable alkaline lysis process, including procedures and devices for the isolation of large quantities (grams and kilograms) of plasmid DNA from recombinant *E. coli* cells. Effective, controllable, and economical operation, and consistent low level of host chromosomal DNA in the final plasmid product. Involves a series of new unit operations and devices for cell resuspension, cell lysis, and neutralization.

20 Claims, 3 Drawing Sheets

OTHER PUBLICATIONS

Durland et al. "Manufacturing and Quality Control of Plasmid-Based Gene Expression Systems." *Advanced Drug Delivery Reviews* 30 (1998) 33-48.

Filtron *Membrane Separation Products Brochure* (1995/96) 1-17.

Goebel, U. et al. "Quantitative Electroeleution of Oligonucleotides and Large DNA Fragments from Gels and Purification by Electrodialysis." *Journal of Biochemical and Biophysical Methods* 14 (1987) 245-60.

Graf et al. "Performance of a Tubular Microporous Membrane Filter Used for In Situ Sampling of Mammalian Cell Culture Medium." *Biotechnology Techniques* 5 (Apr. 1991) 183-6.

Hancher et al. "88983n Evaluation of Ultrafiltration Membranes with Biological Macromolecules." *Biochem. Methods* 79 (Oct. 1973) 165.

Heinzel et al. "Autonomous DNA Replication in Human Cells is Affected by the Size and the Source of the DNA." *Molecular and Cellular Biology* 11 (1991) 2263-72.

Hirt, B. "Selective Extraction of Polyoma DNA from Infected Mouse Cell Cultures." *Journal of Molecular Biology* 26 (1967) 365-9.

Hjerten. "Hydrophobic Interaction Chromatography of Proteins, Nucleic Acids, Viruses, and Cells on Noncharged Amphiphilic Gels." *Methods of Biochemical Analysis* 27 (1981) 89-108.

Horn, N. et al. "Cancer Gene Therapy Using Plasmid DNA: Purification of DNA for Human Clinical Trials." *Human Gene Therapy* 6 (May 1995) 565-73.

Hou, K.C. et al. "Endotoxin Removal by Anion-Exchange Polymeric Matrix." *Biotechnology and Applied Biochemistry* 12 (1990) 315-24.

Hubble et al. "Alginate Ultrafiltration Membranes." *Biotechnology Letters* 7 (Apr. 1985) 273-6.

Ish-Horowicz et al. "Rapid and Efficient Cosmid Cloning." *Nucleic Acids Research* 9 (1981) 2989-98.

Kahn et al. "Purification of Plasmid DNA by Tangential Flow Filtration." *Biotechnology and Bioengineering* 69 (2000) 101-6.

Kasai. "Size-Dependent Chromatographic Separation of Nucleic Acids." *Journal of Chromatography* 618 (1993) 203-21.

Kato. "New Support for Hydrophobic Interaction Chromatography of Proteins." *Journal of Chromatography* 292 (1984) 418-26.

Koller, et al. "Laboratory-Scale Production and Purification of Recombinant HIV-1 Reverse Transcriptase." *Journal of Chromatography* B664 (1995) 107-18.

Lis et al. "Size Fractionation of Double-Stranded DNA by Precipitation With Polyethylene Glycol." *Nucleic Acids Research* 2 (1975) 383-9.

Maa, et al. "Rapid High-Performance Liquid Chromatography of Nucleic Acids With Polystyrene-Based Micropellicular Anion Exchangers." *Journal of Chromatography* 508 (1990) 61-73.

Maniatis. "Large-Scale Isolation of Plasmid DNA," *Molecular Cloning—A Laboratory Manual*. Cold Spring Harbor Laboratory Press: USA (1982) 85, 87, 90, and 91.

Marashi F. et al. "Use of Ultrafiltration Microconcentrators in the Concentration and Desalting of DNA." *BioTechniques* (May/Jun. 1985) 238-40.

Marquet et al. "Characterization of Plasmid DNA Vectors for Use in Human Gene Therapy, Part 1." *BioPharm* (1997) 42-55.

Marquet, et al. "Process Development for the Manufacture of Plasmid DNA Vectors for Use in Gene Therapy." *BioPharm* (Sep. 1995) 26-37.

McLauhlin. "Resolution of RNA Using High-Performance Liquid Chromatography." *Journal of Chromatography* 418 (1987) 51-72.

Merion et al. "Purification of Supercoiled Plasmids from Crude Cell Lysates Using High Performance Anion Exchange Chromatography." *BioTechniques* 7 (1989) 60-7.

Michaels et al. "Chapter 3: Tangential Flow Filtration." *Separations Technology, Pharmaceutical and Biotechnology Applications*. Interpharm Press, Inc.: Buffalo Grove, IL (1995) 57-194.

Montbriand, P.M. et al. "Improved Method for the Removal of Endotoxin from DNA." *Journal of Biotechnology* 44 (1996) 43-6.

Morelle, G. "A Plasmid Extraction Procedure on a Miniprep Scale." *Focus* 11 (1989) 7-8.

Ohmiya, et al. "Separation of DNA Fragments by High-Resolution Ion-Exchange Chromatography on a Nonporous QA Column." *Analytical Biochemistry* 189 (1990) 126-30.

Papamichael et al. "Continuous Aqueous Phase Extraction of Proteins: Automated Processing and Recycling of Process Chemicals." *J. Chem. Tech. Biotechnology* 54 (1992) 47-55.

Prazeres et al. "Large-Scale Production of Pharmaceutical-Grade Plasmid DNA for Gene Therapy: Problem and Bottlenecks." *Trends Biotechnology* 17 (1999) 169-74.

Rembhotkar et al. "Large Scale Preparation of Bacteriophage Lambda by Tangential Flow Ultrafiltration for Isolation of Lambda DNA." *Anal. Biochem* 176 (May 1989) 373-4.

Rippel et al. "Systematic Method Development in Hydrophobic Interaction Chromatography I. Characterization of the Phase System and Modeling Retention." *J. of Chromatography A* 697 (1995) 17-29.

Sharma, S.K. "Endotoxin Detection and Elimination in Biotechnology." *Biotechnology and Applied Biochem* 8 (1986) 5-22.

Solum, N.O. "The Coagulogen of Limulus Polyphemus Hemocytes: A Comparison of the Clotted and Non-Clotted Forms of the Molecule." *Thrombosis Research* 2 (1973) 55-70.

Song et al. "Theory of Concentration Polarization in Crossflow Filtration." *J. of Chem. Society, Faraday Transactions* 91 (1995) 3389-98.

Talmadge, K.W. et al. "Efficient Endotoxin Removal with a New Sanitizable Affinity Column: Affi-Prep Polymyxin." *Journal of Chromatography* 476 (1989) 175-85.

Theodassiou et al. "The Processing of a Plasmid-Based Gene from *E. coli*. Primary Recovery by Filtration." *Bioprocess Engineering* 16: (1997) 175-83.

Thompson, J. A. "A Review of High-Performance Liquid Chromatography in Nucleic Acids Research, III: Isolation, Purification, and Analysis of Supercoiled Plasmid DNA." *BioChromatography* 1 (1986) 68-80.

Vanhaecke, E. et al. "Endotoxin Removal by End-Line Filters." *Journal of Clinical Microbiology* 27 (1989) 2710-2.

Veide et al. "Continuous Extraction of Beta-D-Galactosidase From *E. coli* in an Aqueous Two-Phase System: Effects of Biomass Concentration on Partitioning and Mass Transfer." *Enzyme Microb. Technol.* 6 (1984) 325-30.

Weiss, A.R. et al. "Clearance of Endotoxin from Solution by Adsorptive Filtration with Sartobind Membrane Adsorbers." *Developing Methods $7^{th}$ Ed.*: Sartorius Corp. (1995) 1-7.

Diagen. "Plasmid Midi and Maxi Preparations." *The Qiagenologist, Application Protocols; $3^{rd}$ Ed.* Qiagen, Inc.: Chatsworth, CA (Nov. 1990) 13-4.

Yates et al. "Stable Replication of Plasmids Derived from Epstein-Barr Virus in Various Mammalian Cells." *Nature* 313 (1985)812-5.

Zasloff et al. "A New Method for the Purification and Identification of Covalently Closed Circular DNA Molecules." *Nucleic Acids Research* 5 (1978) 1139-53.

Carlson et al, "Mechanical disruption of *Escherichia coli* for plasmid recovery," Biotechnology and Bioengineering, 48:303-315, 1995. John Wiley & Sons, Inc., USA.

Chandra, G., "Large-scale purification of plasmid DNA by fast protein liquid chromatography using a hi-load Q sepharose column," Analytical Biochemistry, 203: 169-172, 1992.

Coppella, S., "Isolation of high-molecular-weight nucleic acids for copy number analysis using high-performance liquid chromatography," Journal of Chromatography, 402: 189-199.

1987. Elsevier Science Publishers B.V., The Netherlands.

Guide to Tentacle-Biochemistry www.chromatography.co.uk/products/bio/summary.htm, retrieval date: Aug. 26, 2003.

Horn, N., et al., "Cancer Gene Therapy using plasmid DNA: purification of DNA for human clinical trials," Human Gene Therapy, 6:565-573, May 1995. mary Ann Liebert, Inc., USA.

Kahn, et al, "Purification of plasmid DNA by tangential flow filtration," Biotechnology and Bioengineering, 69(1):101-106, 2000. John Wiley & Sons, Inc., USA.

Maniatis, "Large scale isolation of plasmid DNA," Molecular Cloning—a Laboratory Manual, 85,87,90 and 91, 1982. Cold Spring Harbor Laboratory Press, USA.

Marquet, et al., "Characterization of plasmid DNA vectors for us in human gene therapy," Part 1, BioPharm, 42-55, 1992. Biotechniques Press Publishing, USA.

Marquet, "Process development for the manufacture of plasmid DNA vectors for use in gene therapy," BioPharm, 8(7): 34, 1995.

Montbriand, PM, et al, "Improved method for the removal of endotoxin from DNA," Journal of Biotechnology 44: 43-46, 1996. Elsevier Sci. Pub. BV, The Netherlands.

Prazeres, et al., "Large-scale production of pharmaceutical-grade plasmid DNA for gene therapy: problem and bottlenecks," Trends Biotechnol., 17: 169-174, 1999. Elsevier Sci.

Theodassiou, et al., "The processing of a plasmid-based gene from *E. coli*. Primary recovery by filtration," Bioprocess Engineering, 16:175-183, 1997. Springer-Verlag, Germany.

Zasloff, et al, "A new method for the purification and identification of covalently closed circular DNA molecules," Nucleic Acids Research, 5:1139-1153, 1978, Oxford University Press, UK.

Kasai, K, "Size-dependent chromatographic separation of nucleic acids," Journal of Chromatography 618:203-221, 1993. Elsevier Scientific Pub. BV, The Netherlands.

Maa, et al, Abstract, "Rapid high-performance liquid chromatography of nucleic acids with poly-styrene-based micropelicular anion exchangers," Journal of Chromatography A. 508:61-73, 1990. Elsevier Scientific Pub.BV, The Netherlands.

McLaughlin, et al., "Resolution of RNA using high-performance liquid chromatography," Journal of Chromatography, 418:51-72, 1987. Elsevier Scientific Pub. BV, The Netherlands.

Merion, et al., "Purification of supercoiled plasmids from crude cell lysates using high performance anion exchange chromatography," BioTechniques 7(1):60-67, 1989.

Ohmiya, et al., Abstract, "Separation of DNA fragments by high-resolution ion-exchange chromatography on a nonpourous QA column," 189(1):126-130, 1990. Academic Press, USA.

File History of U.S. Appl. No. 09/774,284, filed Jan. 29, 2001, now Patent No. 7,026,468, Issued Apr. 11, 2006.

Kato, Yoshio, "New support for hydrophobic interaction chromatography of proteins," Journal of Chromatography, 292 (1984) 418, Elsevier Science Publishers BV, The Netherlands.

Rippel, Geza, "Systematic method development in hydrophobic interaction chromatography," Journal of Chromatography 697 (1995) 17-29, Elseveir Science BV.

Koller, Gabriele, "Laboratory-scale production and purification of recombinant HIV-1 reverse transcriptase," Journal of Chromatography 664 (1995) 107-118, Elsevier Science.

Kasai, Ken-ichi, "Size-dependent chromatographic separation of nucleic acids," Journal of Chromatography, 61, 1993:203-221 Elsevier Science Publishers, BV.

* cited by examiner

PROCESS AND EQUIPMENT FOR PLASMID PURIFICATION

RELATED APPLICATIONS

This application claims priority to U.S. patent application Ser. No. 09/774,284, filed Jan. 29, 2001 and published Oct. 25, 2001 as 2001/0034435, which claimed priority to U.S. patent application Ser. No. 08/887,673, filed Jul. 3, 1997, now abandoned, which in turn, claimed priority to U.S. Provisional Patent Application Ser. No. 60/022,157, filed Jul. 19, 1996. Both applications are hereby incorporated by reference as if fully set forth herein.

FIELD OF THE INVENTION

The present invention relates to the field of plasmid purification and is particularly useful in the field of gene therapy.

BACKGROUND OF THE INVENTION

The following description of the background of the invention is provided to aid in understanding the claimed invention, but it is not admitted to constitute or describe prior art to the claimed invention and should in no way be construed as limiting the claimed invention.

The traditional alkaline lysis process for isolation of plasmid DNA from bacterial cells is described in Birnboim, H. C. and J. Doly, Nucleic Acids Res. 7:1513, 1979 and is also described in J. F. Burke, Nucleic Acids Res. 8:2989, 1981. It makes use of several laboratory-scale apparatuses and manual operations which are not suitable for large-scale manufacturing. In addition, the traditional alkaline lysis process is not suitable for making pharmaceutical grade material for human use, since inconsistent process performance may result in an unacceptable level of sheared host chromosomal DNA in the final plasmid product. The difficulty of theoretical study of some of the critical parameters for manual operations, like shear force, also make the traditional process unlikely to become a large scale manufacturing process.

Such traditional processes consist of three stages. The first stage is cell resuspension, which normally utilizes manual stirring or a magnetic stirrer, and a homogenizer or impeller mixer to resuspend cells in the resuspension buffer. Manual stirring and magnetic stirring are only appropriate for laboratory scale preparations.

The second stage is cell lysis. It is desirable to minimize shear of host chromosomal DNA at this stage, because it is difficult to remove sheared chromosomal DNA in the downstream purification process (due to the similarity in properties between sheared chromosomal DNA and plasmid DNA). The lysis is normally carried out by manual swirling or magnetic stirring in order to mix the resuspended cells with lysis solution (consisting of diluted alkali (base) and detergents); then holding the mixture at room temperature (20-25 degrees Celsius) or on ice for a period of time, such as 5 minutes, to complete lysis. As noted above, manual swirling and magnetic stirring are not scalable. In addition, it is difficult to optimize the process and obtain consistent process performance due to the number of operation parameters, including operator to operator variability.

The third stage is neutralization and precipitation of host contaminants. Lysate from the second stage is normally mixed with a cold neutralization solution by gentle swirling or magnetic stirring to acidify the lysate before setting in ice for 10-30 minutes to facilitate the denaturation and precipitation of high molecular weight chromosomal DNA, host proteins, and other host molecules. Again, both manual swirling and magnetic, stirring are not scalable. An ice bath is not convenient if a long holding time is desired in a large scale process, because a large quantity of water must be removed and a large quantity of ice/or ice-NaCl mixture needs to be added periodically to maintain a steady temperature.

Once the plasmid DNA is extracted from the lysed cells its purification has become a routine and important procedure for the molecular biologist. However, the scale for these purifications, often referred to as "mini-preps", is usually less than about 1 milligram of plasmid DNA. These small scale preps isolate plasmid DNA from the supernatant of lysed bacterial cells using a variety of techniques, such as ethanol precipitation. For slightly larger scale preparations, the primary techniques employed use cesium chloride centrifugation, binding and eluting to silica resins (in the presence of chaotropic salts) or binding and eluting with various anionic chromatography resins. In addition, other techniques are sometimes used in combination with the resins mentioned, e.g., PEG and/or alcohol precipitation, RNase treatment, and phenol/chloroform extraction. There are also some plasmid purifications performed using analytical HPLC, in particular reverse phase HPLC to separate different plasmid forms using organic solvent systems.

Reverse phase chromatography ("RPC") is generally practiced by binding compounds of interest to a chromatography support in an aqueous solution and eluting with increasing amounts of an organic solvent, such as acetonitrile or alcohol. This approach has been used by a number of investigators to separate DNA, especially oligonucleotides and small (less than 1,000 base pair) restriction fragments. It has also been used to separate open circular and supercoiled plasmids. However, RPC solvents present volatility, fire, health and waste disposal risks. In addition, RPC of nucleic acids frequently requires the use of an ion-pairing agent (e.g., triethylammonium acetate or TEAA) which can be difficult to remove from the DNA and can be toxic to cultured cells.

The "mini-prep" procedures described above were designed for purifying small amounts of plasmid DNA and in general they have not been suitable for large-scale, high throughput purification processes. Large scale purification of plasmid DNA may magnify the contaminants in the final purifications in the final preparations, which usually go undetected in mini-preps. Anion-exchange chromatography as a single chromatography step is unlikely to remove enough of the contaminants which would be necessary for a therapeutic product. Thus, additional processes should probably be included to increase the purity of the plasmid DNA. In addition, it would be useful to have a scalable process which could also resolve various plasmid forms.

Two contaminants which may be particularly troublesome are RNA and chromosomal DNA. Many mini-prep procedures attempt to remove RNA using one or several RNase enzymes which degrade the RNA to ribonucleotides and small oligoribonucleotides. These can then be separated from the plasmid DNA using any of a variety of techniques, including alcohol precipitation, size exclusion chromatography, anion exchange chromatography, etc. However, the use of RNase is undesirable in large scale (equal to or greater than 50-100 mg of plasmid) purification. RNase is an expensive material that is generally not reused. Large scale RNase reactions can be difficult to perform in batch mode with appropriate control of time, temperature and other reaction conditions. Also, RNase is typically isolated from bovine pancreas. As such, it is a possible source of mammalian pathogens, especially retrovirus and bovine spongiform encephalopathy (BSE). Use of such materials in making plasmids for human use presents significant safety and regulatory issues.

Another approach to removal of RNA involves differential precipitations whereby plasmid DNA is precipitated while RNA remains in solution or vice versa. An example is described in WO 95/21250 in which polyethylene glycol (PEG) is used to precipitate RNA from a solution containing both RNA and plasmid. Similar techniques have been described. A disadvantage of these techniques as typically practiced is that the plasmid is first partially purified from the lysate by removing solid debris, precipitated proteins and other solids, and optionally by alcohol precipitation of the nucleic acids (including RNA and plasmid). Differential precipitation is then applied to the partially purified mixture of RNA and plasmid. This approach to differential precipitation has required multiple steps, increasing the time effort and complexity of the process, and introducing more opportunities for loss of plasmid.

Removing chromosomal DNA derived from the bacterial host is also a challenging task in plasmid purification. In a typical "mini-prep", chromosomal DNA is removed primarily during the lysis and neutralization steps. Large fragments of chromosomal DNA are bound to proteins and membrane fragments, and are carried into the precipitate during the neutralization step. However, it is well known that if the chromosomal DNA is sheared to smaller size ($\leq$ about 10 kb), it is not efficiently precipitated and contaminates the plasmid DNA. Thus, it has been assumed that during mini preps, one must avoid vigorous mixing and shearing of the lysate. This is difficult to achieve at larger scales due to the known difficulties of mixing large volumes of liquid. Thus, it is desirable to have a way to separate plasmid DNA from chromosomal DNA subsequent to lysis and neutralization.

One approach to this is CsCl/ethidium bromide density gradients. These are very effective for small amounts of plasmid ($\leq$1 mg) that are not intended for human use. They are not generally suitable for scaling up to over 100 mg lots due to the high cost of necessary equipment. They are also not generally suitable for producing plasmid for human use because ethidium bromide binds tightly to DNA, is difficult to remove quantitatively, and is a known mutagen and suspected carcinogen.

Thus, there are several clear needs for large scale plasmid purification. These include a method to mix large volumes of lysate with low shear, a method to precipitate RNA directly from a lysate without prior additional purification, and a method to separate sheared chromosomal DNA from plasmid DNA.

Other methods for purification of larger amounts of plasmid DNA are not ideal and leave significant room for improvement. For example, the method described in WO 95/21250, published Aug. 10, 1995 involves multiple precipitations, plasmid precipitations, low capacity size exclusions, and requires flammable alcohols. Similarly, the method described in WO 96/02658, published Feb. 1, 1996, requires lysozyme, may require RNase, and requires flammable alcohols.

SUMMARY OF THE INVENTION

The present invention relates to a scalable alkaline lysis process, including procedures and devices for the isolation of large quantities (grams and kilograms) of plasmid DNA from recombinant *E. coli* cells. The present invention provides effective, controllable, and economical operation, and consistent low level of host chromosomal DNA in the final plasmid product. These attributes, and the details which follow, clearly provide advantages over the traditional alkaline lysis process and the methods proposed by others for commercial scale procedures.

The present invention exploits a set of devices and procedures capable of providing fast and efficient cell resuspension in a semi-continuous mode. All device's design and operation parameters can be well characterized and optimized through empirical tests in both scale-down and scale-up processes. Both mixing quality and shear force can be well controlled to maximize mixing efficiency and to minimize possible damage to cells.

The present invention also provides a set of devices and procedures capable of providing efficient and gentle mixing and cell lysis in a continuous flow mode. The device's design (e.g. device dimension) and operation parameters (e.g. flow rate and residence time) were well characterized through empirical tests and theoretical calculations and modeling to maximize lysis efficiency and minimize shearing of chromosomal DNA. Surprisingly, by performing alkaline lysis using a high concentration of unbuffered salt, not only is denatured chromosomal DNA, protein, and cellular debris trapped in a precipitable salt/detergent complex, but a significant portion of RNA is also precipitated, thereby eliminating the need for an RNase treatment step and providing a significant advantage.

In addition, the present invention provides a set of devices and procedures capable of providing fast chilling and efficient and gentle mixing to denature and precipitate chromosomal DNA, protein, and RNA. The devices' selection and design and operation parameters were well characterized through scale-up-empirical testing.

The invention relies, in part on the use of anion exchange chromatography, preferably with a Fractogel EMD 650S TMAE(S) resin with a 20-40 micron size. Other tentacle resins or means for making binding sites more available to larger molecules like plasmids can also be used. The tentacles are preferably 15 to 50 units in length and have an average of 18 charged groups covalently bound to each tentacle. TMAE Fractogel 650S is a tentacle ion exchanger having trimethylaminoethyl functional groups (TMAE) covalently attached to hydroxyl groups of a synthetic methacrylate based polymeric resin backbone.

The use of such resins: (1) provides a high plasmid DNA binding capacity (about 3 mg/mL, preferably about 1.5 mg/mL); (2) allows for efficient removal of proteins, RNA, low molecular weight molecules and probably some chromosomal DNA and some open circle plasmid DNA; and (3) provides a means for enriching the supercoiled plasmid DNA above about 80% using a step gradient. Supercoiled plasmid binds tighter to the Fractogel resin (high affinity sites) allowing the remaining RNA and some open circle plasmid to be removed.

The invention also relies in part on the use of hydrophobic interaction chromatography, which is used to separate plasmid DNA from *E. coli* chromosomal DNA and RNA and may also be used to separate open circular plasmid DNA from supercoiled DNA. Overall, HIC is a powerful technique for plasmid DNA purification. This disclosure reveals the surprising and unexpected value that hydrophobic interaction chromatography (HIC) has, especially when used in conjunction with anion-exchange chromatography, for large-scale plasmid DNA purification. Particularly surprising is the ability of HIC to resolve the supercoil form of a plasmid from the relaxed open circle form. Supercoiled DNA may be easier to formulate and with certain formulations supercoiled plasmid may have higher expression levels in vivo (e.g., about 10 times greater expression in certain systems). Another surprising and important fact is that removal of chromosomal DNA, denatured plasmids, RNA, and endotoxin from the plasmid DNA forms can also be achieved.

Thus, in one aspect the invention provides a process for isolating a large quantity (e.g. gram or kg amounts) of plasmid DNA. The method involves the steps of: (a) lysing cells containing the plasmid DNA with a lysis agent, thereby forming a lysate; (b) treating the lysate with a high salt agent that preferably is capable of forming a precipitable complex with non-plasmid DNA cellular components contained in the lysate, thereby forming a treated solution; and (c) purifying the treated solution to provide isolated plasmid DNA.

The phrase "plasmid DNA" is meant to include all forms of plasmid DNA, such as supercoiled plasmid DNA (type I), nicked circle plasmid DNA (type (II), and linearized plasmid DNA (type III), as well as denatured plasmid DNA. The plasmids may include any of a wide variety of vectors, origins of replication, and genetic elements (such as selectable genes, polylinkers, promoters, enhancers, therapeutic genes, leader peptide sequences, introns, polyadenylations signals, etc.) known to those skilled in the art. Genes encoding diverse proteins (including therapeutic proteins such as IL-2, IL-12 and the like) may be inserted into the plasmid, and the genes may constitute, for example, genomic DNA, cDNA, synthetic DNA, and polynucleotide and oligonucleotide sequences.

By "lysis agent" is meant any agent capable of breaking open a cell containing plasmid DNA and thereby releasing the contents of the cell. The lysis agent preferably is alkali or basic, i.e., it has a pH above 7.0, preferably about 12 to 13. Many suitable agents are known to those in the art, for example, a solution containing 0.2N sodium hydroxide in 1% SDS. Other concentrations of sodium hydroxide in SDS may also be used. Other detergents (tween, np40, sarkosyl, etc.) such as non-ionic detergents (e.g., triton X) and lysozyme plus heat treatment may all also be used.

By "high salt agent" is meant a substance that is capable of precipitating out a significant portion (preferably at least 25%, more preferably at least 50%, most preferably at least 75% or 90%) of any RNA molecules released from the cells. The high salt agent preferably has one or more salts at a pH above approximately 5.5, for example a mixture of 1M potassium acetate and 7M ammonium acetate at a pH between 7.0 and 9.0. It may be possible to replace the potassium acetate with a potassium agent or ion and/or KCl, NaCl, or $NH_4OAc$. The lysate is preferably treated with the high salt agent for at least six hours at approximately four degrees Celsius.

In preferred embodiments, the process does not involve the use of RNase, the process yields isolated plasmid DNA that is pharmaceutical-grade plasmid DNA suitable for administration to humans, and at least 100 milligrams of the isolated plasmid DNA is obtained, more preferably at least 1 g, most preferably at least 10 g, 100 g or 1,000 g (1 kg). In other preferred embodiments, the invention provides a process for isolating plasmid DNA involving the steps of: (a) resuspending cells in approximately 50 mM of Tris-HCl buffer at a pH of about 8.0 and approximately 10 mM $EDTA(Na)_2$; (b) lysing cells containing the plasmid DNA with a lysis agent comprising an approximately equal volume of 0.2N sodium hydroxide in 1% SDS, thereby forming a lysate; (c) treating the lysate with a high salt agent that comprises a mixture of 1M potassium acetate and 7M ammonium acetate at a pH between 7.0 and 9.0, preferably capable of forming a precipitable complex with non-plasmid DNA cellular components contained in the lysate, thereby forming a treated solution; and (d) purifying the treated solution to provide isolated plasmid DNA. Step (d) may involve subsequently isolating from the supernatant of the cellular lysate a sample of highly purified supercoiled plasmid DNA.

In view of the above, it can be seen that, among other things, the invention provides an improved process for isolating plasmid DNA from alkaline lysates of a cell containing the plasmid DNA by treating the lysate with a high salt agent, preferably capable of forming a precipitable complex with non-plasmid DNA cellular components contained in the lysate.

In another aspect, the invention provides a process for isolating plasmid DNA involving the steps of: (a) lysing cells containing the plasmid DNA with a lysis agent, thereby forming a lysate; and (b) purifying the lysate with anion exchange chromatography using a step gradient, thereby producing isolated plasmid DNA enriched with at least 80% supercoiled plasmid DNA.

In preferred embodiments the anion exchange chromatography is performed with a resin having a particle size of 20-40 microns, the anion exchange chromatography has a plasmid DNA binding capacity of about 1.5 mg of plasmid per mL of resin, more preferably a plasmid DNA binding capacity of about 3 (or more) mg of plasmid per mL of resin, and the anion exchange chromatography is performed with a Fractogel EMD TMAE (650-S) resin. Thus, the invention provides an improved process for isolating plasmid DNA from lysate of cells containing the plasmid DNA by purifying the lysate with anion exchange chromatography using a step gradient, thereby producing isolated plasmid DNA enriched with at least 80% supercoiled plasmid DNA.

In another aspect, the invention features a process for isolating plasmid DNA involving the steps of: (a) lysing cells containing the plasmid DNA with a lysis agent, thereby forming a lysate; and (b) using hydrophobic interaction chromatography (HIC) to purify the lysate, thereby providing isolated plasmid DNA. Typically the lysate is not applied directly to the HIC column directly, but is first sent through an anion exchange chromatography resin, such as the Fractogel TMAE resin discussed herein.

In preferred embodiments the hydrophobic interaction chromatography is performed with at least 1.6M ammonium sulfate (at 2.0M ammonium sulfate the supercoiled plasmid binds to the HIC column), Tris, and EDTA, and the hydrophobic interaction chromatography is performed with an Octyl Sepharose 4 FF resin. This is a flow through column that allows supercoiled plasmid to flow through the column while RNA, and chromosomal DNA endotoxin and denatured DNA binds to the resin. The column is moderately hydrophobic due to octyl alkyl chains as its ligand on agarose beads. Other resins having similar properties such as phenyl sepharose, butyl sepharose, and others, may also be used.

In other preferred embodiments the plasmid DNA is not precipitated and the process involves no linear gradients and uses no organic solvents, the isolated plasmid DNA is substantially free of endotoxins (for example, 10 to 100 Endotoxin Units per mg of plasmid DNA as measured with a Limulus Amebocyte Lysate Assay) and host cell chromosomal DNA (for example, about 1% to 3% as measured by LCR), the plasmid DNA is not exposed to acidic pH or elevated temperatures (e.g., about pH 8 and 22° C.), the isolated plasmid DNA is produced in a yield of at least 60% (preferably 70%, more preferably 80%, most preferably 90%), the hydrophobic interaction chromatography is performed in an aqueous solution containing a high concentration of salt, such as 1.6M ammonium sulfate, and the cells are recombinant *E. coli* cells. Thus, the invention features an improved process for isolating plasmid DNA from a lysate of a cell containing the plasmid DNA by using hydrophobic interaction chromatography to purify the lysate, thereby providing isolated plasmid DNA. Preferably the lysate is first partially purified with anion exchange chromatography, for example with a TMAE resin, and then the anion exchange chromatography pool, (for example, a TMAE pool) is further purified with HIC.

In yet another aspect, the invention provides a device for isolating plasmid DNA from cells containing the plasmid DNA, comprising: (a) a means for providing cell resuspension in a semi-continuous mode; (b) a means for providing mixing and cell lysis in a continuous flow mode; and (c) a means for providing chilling and mixing to denature and precipitate chromosomal DNA, protein, and RNA.

In preferred embodiments, the means for providing efficient and gentle mixing and cell lysis in a continuous flow mode comprises an impeller mixer, an in-line static mixer, and/or a lysis coil. The device preferably has a means for performing hydrophobic interaction chromatography and the means for providing fast chilling and efficient and gentle mixing to denature and precipitate chromosomal DNA, protein, and RNA preferably comprises a chilled jacketed tank.

Other and further objects, features, and advantages will be apparent from the following description of the drawings and the presently preferred embodiments of the invention, as well as the examples provided herein.

DESCRIPTION OF THE PREFERRED EMBODIMENTS

Figure 1:
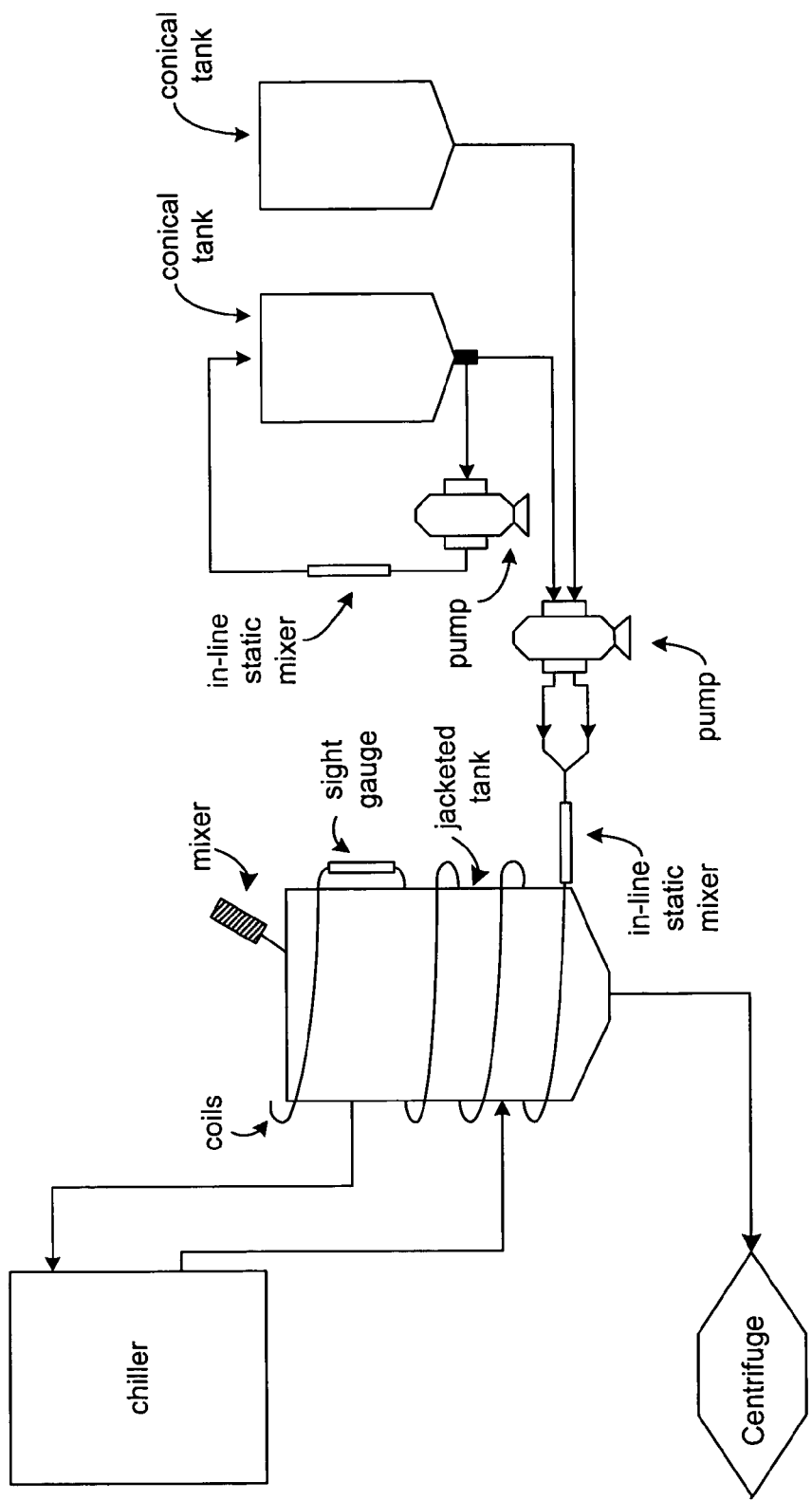
FIG. 1 is a schematic process diagram including resuspension and lysis (in line mixer), and neutralization (impeller mixer).

The invention identified here is a novel, scalable, and alternative alkaline lysis process for large scale plasmid DNA isolation. The present invention involves a series of new unit operations and devices for cell resuspension, cell lysis, and neutralization. The invention can provide controllable and efficient operation and consistent performance and is economical. Described below are various preferred methods for performing the invention as well as a detailed description of the devices and certain aspects of the invention.

The most preferred embodiments are described immediately below, followed by a discussion of several of the steps and devices that may be useful in practicing the invention.

One of the preferred embodiments involves the use of a continuous flow device with in-line mixing for resuspending bacterial cells, lysing with alkali and detergent, and neutralizing the lysate. This has several advantages (relative to batch operation in multiple bottles or large tanks), including: (1) better cell resuspension and mixing of solutions; (2) better control of lysis times; and (3) lower shear, proving less chromosomal DNA contamination (very significant).

A second preferred embodiment involves the use of a modified, non-acidic neutralization solution that can be added to an alkaline/detergent lysate to precipitate RNA as well as chromosomal DNA, protein, lipids, etc. from the lysate. Some of the advantages (relative to 3M potassium acetate, pH ~5) are: (1) removes majority of RNA (especially high molecular weight) prior to column chromatography (very significant); (2) eliminates exposure of plasmid DNA to damaging acid; (3) eliminates need to partially purify plasmid prior to RNA precipitation.

A third preferred embodiment involves the use of Fractogel EMD TMAE tentacle ion exchange resin to separate supercoiled plasmid from open circular plasmid and from protein and low molecular weight RNA. Here, the advantages (relative to Sepharose Q or other low pressure ion exchange resins) include: (1) higher capacity (1.5 mg plasmid/mL resin); (2) high flow rate; (3) able to separate supercoiled and open or nicked circular plasmid using a simple, convenient, scalable salt step gradient (very significant).

A fourth preferred embodiment involves the use of hydrophobic interaction chromatography (HIC) to separate plasmid DNA from chromosomal DNA, RNA, protein, endotoxin, and denatured plasmid DNA. The advantages of this embodiment include: (1) removes *E. coli* DNA (very significant); (2) removes residual RNA, endotoxin, and denatured plasmid DNA; (3) optionally separates supercoiled from nicked or open circular plasmid.

The fifth preferred embodiment is an integrated processes employing some or all of the above (Process I, Process II, and potential variants).

Alkaline Lysis

Conventional alkaline lysis techniques involve the use of 3M potassium acetate at a pH of about 5.5. A significant improvement presented herein is the use of high concentrations of unbuffered salt. (A number of monovalent salts are suitable and some divalent salts will also have acceptable solubility properties.) For example, by adding a volume of an unbuffered solution of 1M potassium acetate and 7M ammonium acetate and letting the mixture stand for at least 2 (preferably at least 6) hours at 4 degrees Celsius a surprising and unexpected result is achieved. Namely, not only is denatured chromosomal DNA, protein, and cellular debris trapped in a precipitable salt/detergent complex, but a significant portion of RNA is also precipitated, allowing for the elimination of an RNase treatment step. The potassium acetate preferably is present in an excess in order to aid in the precipitation the SDS DNA complex. Furthermore, the RNA that remains in solution is typically low molecular weight and can be separated from plasmid DNA by subsequent chromatographic steps (e.g., anion exchange, HIC, size exclusion, etc.). At lower dilutions to the TMAE load (1.5 vs. 3 or 4 volumes), the majority of RNA that remains flows through the TMAE column.

Anion Exchange Chromatography

The present invention makes use of anion exchange chromatography, preferably with a resin such as Fractogel EMD TMAE(s) 650-S having a 20-40 micron particle size. This advantageously provides a high DNA binding capacity of about 3 mg/mL, preferably about 1.5 mg/mL and allows for the efficient removal of proteins, RNA, low molecular weight molecules, and probably some chromosomal DNA. Surprisingly, this invention allows for the enrichment of supercoiled form of plasmid DNA by over 80% using a step gradient. Enrichment of supercoiled plasmid is achieved by removal of more open circular plasmid than is achieved in the preferred embodiment of Process I outlined in FIG. 2. The percentage of enrichment may be measured with a 1% reliant gel (FMC), 0.8% agarose gel electrophoresis, and may also be measured using an ion exchange HPLC assay using, for example, a DEAE column.

Hydrophobic Interaction Chromatography

Hydrophobic interaction chromatography ("HIC") is generally practiced by binding compounds of interest in an aqueous solution containing high concentrations of salt (e.g. ammonium sulfate). Elution is accomplished by lowering the salt concentration. No volatile or flammable organic solvents are used, and no organic modifiers like TEAA are generally required.

There are a variety of HIC resins which are commercially available, differing in both backbone and functional chemistries. In general, they can be made to work for plasmid DNA purification, however there are some which are preferred. The HIC step is a flow through step, i.e., the supercoiled and open circular plasmid flow through the column while RNA, chromosomal DNA, denatured plasmid DNA and endotoxins are retained on the column.

The HIC resins are initially equilibrated in high ionic strength multivalent salts such as ammonium sulfate. These conditions enhance hydrophobic interaction and thus retention of various biomolecules. By reducing the salt concentration the hydrophobic interaction is lessened and the biomolecules begin to elute from the resin depending on their hydrophobicity. In the case of plasmid DNA, it has been observed that the relaxed open circle form has very little interaction with HIC resins in the presence of high salt. While under these conditions the supercoiled form does interact and is retained by the resin leading to a resolution of the forms. As the salt concentration is lowered, the supercoiled form is eluted, while the RNA, chromosomal DNA and denatured plasmid DNA remain bound. Thus, the supercoiled plasmid may be purified from undesired plasmid forms (open circular, denatured) and from contaminants (chromosomal DNA, RNA, protein, endotoxin) using HIC. This is an unexpected result.

The interaction of biomolecules with the HIC resins can also be modified as a function of the multivalent salt selected. It has been observed that in general sodium citrate and potassium phosphate salts can increase hydrophobic interaction of plasmid DNA greater than ammonium sulfate. Thus, by optimizing the selection of resin and salt conditions, one can affect the quality of purification for a given plasmid construct.

Devices

All devices described in this invention were built to large scale (process capacity is greater than 2 kg of wet cell paste) to demonstrate the feasibility and effectiveness of the invented devices and operation procedures, and the concept of continuous-flow-through resuspension, lysis, and neutralization. A polypropylene or stainless steel conical tank with a bottom three-way valve was connected to two sets of platinum-cured silicone tubing. Those skilled in the art will recognize that many other types of containers and/or connections may be substituted without substantially changing the function, mode of operation or result obtained the overall device. One set of tubing contained one unit of ½" in-line static mixer and two units of ⅜" in-line static mixers. These in-line mixers are for resuspending cells and homogenizing cell concentration. Other sizes and numbers of mixers may also suitably be used. The other set of tubing is used to transfer resuspended cells to contact lysis solution.

A MasterFlex peristaltic transfer pump was used for resuspension and homogenization. Other suitable (exp-low shear) pumps are available and may be substituted without materially altering the overall device. A 43 ft×1" OD stainless steel tubing was coiled with approximately 2' diameter and a 6" pitch and used as the lysis coils. Those skilled in the art will recognize that the exact length, diameter, and pitch may be varied by at least 10% and perhaps even over 50% without departing from functional lysis goal served by the coils. The bottom of the lysis coils was connected to a 1" in-line static mixer (multiple mixers may be used) which is used to mix resuspended cells and lysis solution. A MasterFlex peristaltic pump with two stacked pump heads is used to transfer resuspended cells and lysis solution to the 1' in-line static mixer for mixing. As noted above, other pumps and mixers may also be used.

The holding tank for precipitation is a 150 L stainless steel jacketed tank. Other suitable containers will preferably have a volume of at least 100-200 L or more. The tank jacket was connected to a recirculating chiller which has the ability to chill the coolant to −15° C. Other chilling means may be substituted and preferably have the ability to achieve at least 10 degrees Celsius, more preferably zero degrees or lower. Since two approaches were adopted to mix lysate and neutralization solution, two sets of operations and devices were used to accomplish the mixing of lysate and neutralization solution. In the first approach, the effluent of the lysis coils went directly into the chilled tank. An impeller mixer was used to mix lysed cells and neutralization solution inside the tank. The second approach involves a 1" or 2" (or other conveniently sized) in-line static mixer. Lysed cells and neutralization solution were pumped into the in-line static mixer simultaneously (one skilled in the art will recognize that cells or lysis solution could be pumped first, followed by the other), and the effluent of the mixer was directed into chilled tank for precipitation.

It is possible to run the EM Merck Fractogel EMD 650(s) TMAE column in a displacement mode where super coiled plasmid displaces open circular plasmid off the resin, thereby enriching for super coiled plasmid. The column is equilibrated in 0.5M NaCl, TE buffer, the load (neutralized lysis supernatant process 2) is diluted with 1.5 volumes WFI then loaded onto the column. The column is loaded at 3.0 mg/ml resin. The last quarter of the flow through of the load to the TMAE column is recirculated over the column to allow SC plasmid to compete off open circular plasmid. The column is then washed to baseline with 0.5M NaCl, TE after the recirculation has finished. The plasmid is then eluted with 1.9M $(NH_4)_2SO_4$.

Another resin from EM that displays similar properties. The resin is a Fractogel (R) EMD TMAE Hicap (M). This is a high capacity resin with better flow characteristics than the (S) TMAE resin. This Hicap resin may allow binding plasmid between 3 and 5 mg/ml of resin and allow for the enrichment of SC plasmid at a very high level.

EXAMPLES

The following examples are solely for illustrative purposes and are not meant to limit the scope of the invention.

Example 1

Process I

Figure 2:
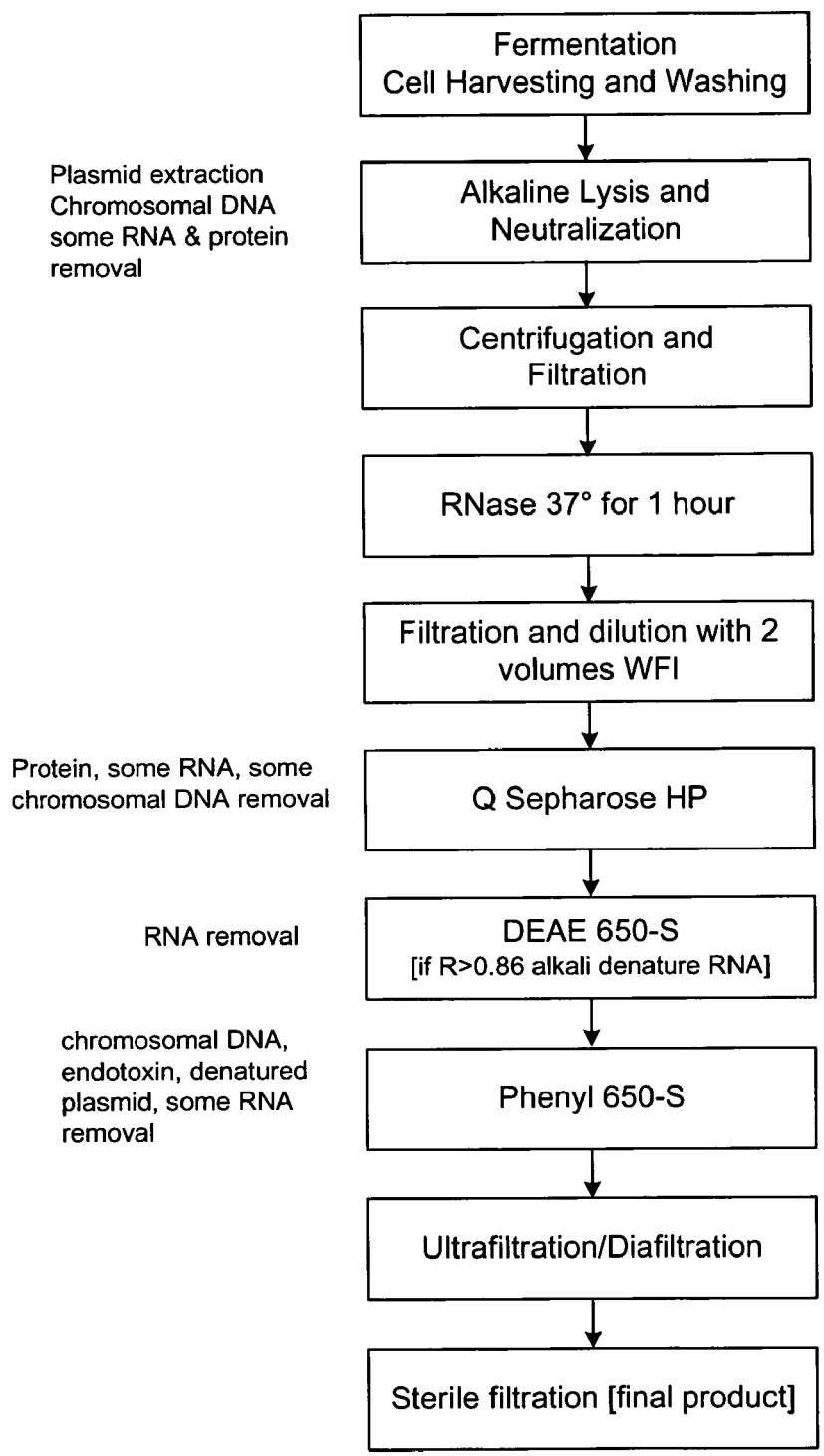
FIG. 2 is a flow chart for Process I.

The step-by-step methodology of Process I is outlined in FIG. 2.

Step 1 involves fermentation, cell harvesting, and washing. These are well known procedures that may be carried out in wide variety of ways known to those skilled in the art.

Step 2 involves alkaline lysis and neutralization. This step extracts plasmid, chromosomal DNA, RNA and protein. As explained in detail above, use of a high concentration of buffered salts is preferable.

Step 3 involves centrifugation and filtration. These also are well known techniques that may be performed in a variety of ways known to those skilled in the art.

Step 4 is RNase treatment at 37 degrees Celsius for one hour. This step may optionally be removed (as in Process II described in Example 2 below) by utilizing the preferred alkaline lysis and high salt agents described herein.

Step 5 involves filtration and dilution with 2 volumes of WFI. These are standard techniques that may easily be modified by those skilled in the art.

Step 6 involves the use of a Q Sepharose HP column to remove protein, and some RNA and chromosomal DNA. Other Q resins may also work, or a Fractogel TMAE resin may be used as in Process II below.

Step 7, involves the use of DEAE 650-S to remove RNA.

Step 8 uses Phenyl 650-S to remove chromosomal DNA, endotoxin, denatured plasmid, and some RNA. Other phenyl resins and 8 carbon octyl resins may also be used.

Steps 9 and 10 are ultrafiltration/diafiltration and sterile filtration to yield the final product. These are common procedures that may be insubstantially modified by those skilled in the art without departing from the scope of the invention.

Example 2

Process II

Figure 3:
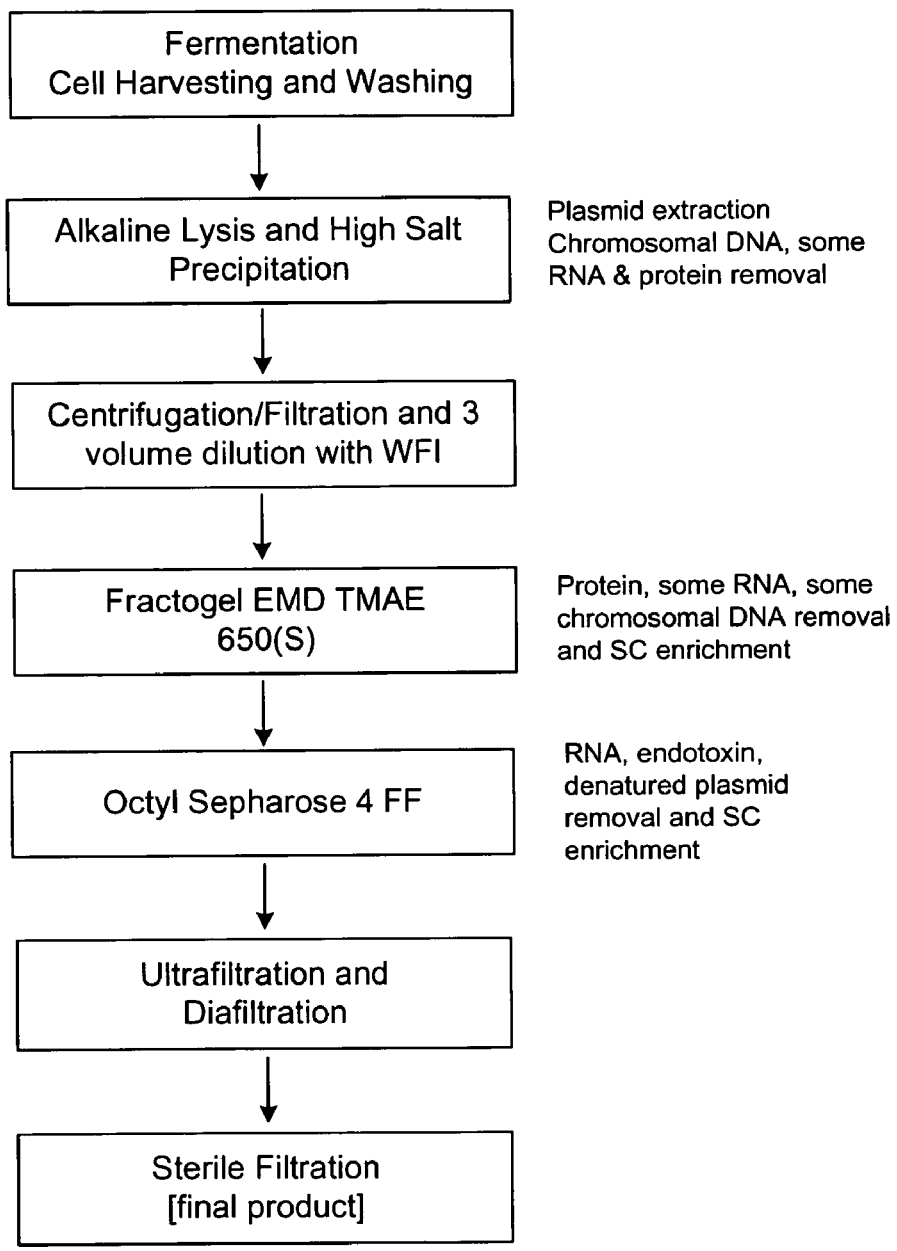
FIG. 3 is a flow chart for Process II.

The steps of Process II are outlined in FIG. 3. Step (a) is fermentation of plasmid containing $E.$ $coli$, cell harvesting, e.g. by centrifugation and washing and resuspending cells as in step 1 of Process I.

Step (b) is alkaline lysis (e.g., 1% SDS and 0.2N NaOH) and high salt precipitation to extract plasmid and remove chromosomal DNA and some RNA and protein. The high salt precipitation may involve adding 1M potassium acetate and 7M ammonium acetate (concentrations of both may be varied, with higher concentrations of ammonium acetate being better for RNA precipitation) and holding the temperature at 4 degrees Celsius for approximately 6 to 12 hours to precipitate RNA (times and temperatures may be varied; lower temperatures and longer times improve precipitation and incubation at 4 degrees Celsius provides a higher percentage of precipitation). The ability to precipitate RNA during neutralization of the alkaline lysate helps eliminate the need for RNase. The acetate solution does not need to be pH adjusted and the pH is approximately 8. Conventional techniques using 3M potassium acetate at pH 5 are dramatically less effective at RNA precipitation and provide greater risk of DNA damage.

Step (c) is centrifugation/filtration and 1.5 volume dilution with water for irrigation (WFI).

Step (d) involves the use of, for example, Fractogel EMD TMAE 650(s), a strong anionic change resin, to remove residual protein and some RNA and chromosomal DNA and enrich the supercoiled form of the plasmid DNA. This resin is capable of separating nicked/relaxed plasmid from supercoiled plasmid with a preparative, low pressure, step elution. Variations in particle size and chemistry may be acceptable. The next procedure is to wash the nicked and/or relaxed circular plasmid, as well as residual RNA, off of the resin with ~0.6M NaCl (10 mM Tris, 1 mM EDTA, pH 8.0). The supercoiled plasmid thus remains bound to resin. Other salts may also be suitable at an appropriate concentration (depending on the salt). This is followed by eluting the covalently closed supercoiled plasmid off of the resin with about 1.9M ammonium sulfate (A.S.). Elution with concentrated A.S. allows eluate to flow through the next column. Elution with $\geq 0.7M$ NaCl is also suitable, but in that case the eluate must be adjusted to ~1.6 M.A.S. prior to the next column. Other salts may also be suitable at an appropriate concentration (depending on the salt).

Step (e) involves the use of Octyl Sepharose 4FF for removal of chromosomal DNA, RNA, endotoxin, and denatured plasmid. This involves passing the TMAE pool through an Octyl Sepharose 4 Fast Flow (Pharmacia #17-0946) resin and collecting the flow through fraction. Other hydrophobic interaction (HIC) resins may also be used (e.g. Pharmacia Phenyl Sepharose, Pharmacia Butyl Sepharose, similar resins from other vendors). At ~1.6M ammonium sulfate, plasmid flows through and residual RNA, endotoxins, and $E.$ $coli$ DNA bind. Alternatively, one can bind the TMAE pool in the presence of ~2.0M ammonium sulfate, which allows relaxed and/or nicked circular plasmid to flow through, while the supercoiled plasmid binds; the supercoiled can then be eluted with $\leq 1.6M$ ammonium sulfate. Variations in resin particle size, etc., may be acceptable and some alternative salts are also suitable at appropriate concentrations.

Steps (f) and (g) are ultrafiltration/diafiltration followed by sterile filtration to yield final product.

Some of the advantages of Process II are listed below: (1) Can enrich/resolve for supercoiled plasmid DNA; (2) Plasmid DNA is never precipitated; (3) No linear gradients necessary; (4) No organic solvents used; (5) In preferred embodiments in Process I, 1.62 volumes of lysis solution (neutralizing) is used whereas in preferred embodiments of Process II, 1 volume of lysis solution (high salt 1M potassium acetate and 7M $NH_4OAc$) is used; (6) No RNase required; (7) Significantly reduces endotoxin levels; (8) DNA is not exposed to either acid pH or elevated temperatures; (9) Scaleable for Industrial Quantities; and (10) High plasmid DNA yields (60-90%) and high purity (90-95%).

Example 3

Unit Operations of the Invention

The unit operations in this invention are in-line static mixers, flow through lysis coils, and a chilled jacketed tank.

The cell paste, either from direct isolation from fermentation or thawed if frozen, was resuspended in TE buffer (50 mM Tris and 10 mM EDTA) by circulating the cell-buffer mixture through the in-line static mixer in a pump-around mode. The flow rate was specifically determined to be capable of effectively resuspending cells without breaking them.

The resuspended cells were mixed with the lysis solution (200 mM NaOH and 1% SDS) by flowing through the in-line static mixer, then entering the lysis coils for continuous lysis at a constant rate. The optimal flow rate to deliver cell-lysis solution mixture through the static mixer and lysis coils was determined to maximize the flow rate, minimize the shear force, and generate homogeneous mixture and desired molecule residence time.

The lysate was mixed with cold neutralization solution (1.85M KOAc, 1.16N $NH_4OAc$, and 1.15M NaCl pH 5.5 Process I buffer solution) to denature and precipitate high molecular weight host chromosomal DNA, host proteins, and host RNA. The mixing of neutralization solution and lysate is either accomplished by flowing through the in-line static mixer in a continuous mode, or by agitating the low speed impeller mixer in a batch mode.

After mixing, the acidified lysate will be retained in the chilled jacketed tank for 20-30 minutes to complete the precipitation and denaturation.

Example 4

Scale-Up Test

The scale-up test was started from transferring thawed cells and TE buffer into the conical tank. The cell-TE mixture was then pumped through the in-line static mixer to the optimized flow rate. After completing cell resuspension, cells and lysis solution were pumped through another in-line static mixer simultaneously for mixing. At the same time of mixing cells and lysis solution, cells remained in the conical tank were still circulated through the resuspension-in-line static mixer to ensure the homogeneity of cell pool to maximize the effectiveness of alkaline lysis. Lysate continuously flowed through the lysis coils at a fixed residence time.

The effluent from the lysis coils was directed to a chilled jacketed tank containing a high salt neutralizing solution and equipped with an impeller stirrer for mixing for mixing. However, the preferred method would be to mix the highly viscous alkaline cell lysis solution with the much lower viscosity high salt solution using an in-line static mixer to minimize the shearing of the chromosomal DNA. This would allow for instantaneous mixing of the two solutions in a gentle manner to form the denatured chromosomal DNA/denatured protein/sodium dodecyl sulphate complex. Afterwards the neutralized precipitated lysate would be directed to a cold jacketed holding tank.

Example 5

Isolation of Plasmid 1.5 kg (wet weight) of frozen recombinant *E. coli* cells harboring a plasmid was thawed and TE buffer was added to make a total volume to 10.5 L. The mixture of cell paste and TE buffer was circulating through the in-line mixers at 3 L/min for 5-10 minutes at room temperature to obtain homogeneous cell concentration. The resuspended cells and room temperature lysis solution were pumped to the 1" in-line static mixer simultaneously at an overall flow rate of 1.0 L/min. The mixture of cells and lysis solution continuously flowed through the lysis coils at 1.0 L/min.

The lysate exiting from the lysis coils directly into the jacketed tank which contained 17 L cold neutralization buffer. The lysate and cold neutralization solution were gently mixed by an impeller mixer to avoid shearing the host chromosomal DNA. The acidified lysate was kept in the chilled-jacketed tank for about 30 minutes to completely precipitate the host chromosomal DNA, host proteins, and host RNA.

After completing the precipitation, plasmid was isolated and purified. The host chromosomal DNA level in the final product was assayed at 0.4%.

Example 6

Reproducibility of the Alkaline Lysis Process 1.5 kg (wet weight) of frozen recombinant *E. coli* cells harboring a plasmid was used to examine the reproducibility of the invented process. All buffers, devices, and procedures were adopted to mimic Example 5. The isolation and purification procedures were also the same as that used in Example 5. The host chromosomal DNA level in the final product was assayed at 0.12%.

Example 7

Variability of Final Product Quality

|  | Without Use of Device | With Use of Device |
| --- | --- | --- |
| Number of Lots Used for Comparison | 37 | 7 |
| Average Chromosomal DNA, % | 2.83 | 0.63 |
| Standard Deviation | 2.68 | 0.64 |

The above showed that the use of the device is superior in regard to both final product quality (chromosomal DNA level) and process performance consistency.

Example 8

Purification of Plasmid DNA Containing the $\alpha 1$-Antityrpsin Gene

Previous purification of an $\alpha_1$-antitrypsin plasmid prep had been done by the process 1 protocol (FIG. 1) in which the H.I.C. step had not yet been incorporated. Thus the purification process ended after the DEAE column step and the resulting plasmid pool was concentrated by standard ethanol precipitation. The final product of $\alpha_1$-antitrypsin plasmid prepared by the above method still contained unacceptable high levels of chromosomal DNA (bacterial), RNA, denatured plasmid, and endotoxins.

Therefore a phenyl hydrophobic interaction chromatography (HIC from TosoHaas) step was added to the process 1 protocol following the DEAE chromatography column in order to reduce the contaminants to a much lower level and thereby increasing the purity of the plasmid DNA to a level $\geqq$ 95%.

Approximately 315 grams of DH-5$\alpha$ *E. coli* cells (wet weight) containing the $\alpha_1$-antitrypsin plasmid was exposed to alkaline lysis for 5 minutes and the denatured chromosomal DNA/protein/sodium dodecylsulfate complexes were precipitated by addition of a salt solution containing 1.85M potassium acetate, 1.15M sodium chloride, 1.16M ammonium acetate at pH 5.5. After centrifugation, filtration, and RNAse treatment the resulting supernatant (8 L) contained ~35 µg plasmid DNA/mL.

Following anion exchange chromatography of the lysate on both Q Sepharose 4FF (Pharmacia) and DEAE 650-S (TosoHaas) which removes protein, RNA and the bulk of chromosomal DNA, the plasmid pool was then pumped onto a phenyl 650-S (TosoHaas) HIC resin.

The phenyl 650-S resin (100 mL) was packed into a 5 cm diameter column to a height of 5 cm. The column was equilibrated with approximately 500 mL of 1.75M $(NH_4)_2SO_4$ at 20 mL/minute. Then 350 mL of the DEAE elution pool containing the $\alpha_1$-antitrypsin plasmid was diluted with an equal volume of 3.5M $(NH_4)_2SO_4$ which results in a final concentration of 1.75M $(NH_4)_2SO_4$. The entire 700 mL of plasmid DNA in 1.75M $(NH_4)_2SO_4$ was pumped through the HIC column and the flow through peak which contains the $\alpha_1$-antitrypsin plasmid was saved for further processing by ultrafiltration and diafiltration (UF/DF). The bound RNA, chromosomal DNA, denatured plasmid and endotoxins were eluted in a Milli-Q water wash followed by a 70% ethanol (v/v) wash.

A Pellicon-2 system (Millipore) containing a 50 kD casseter (Millipore) was used to UF/DF the HIC flow through containing the $\alpha_1$-antitrypsin plasmid DNA in 1.75M $(NH_4)_2SO_4$. The final product ($\alpha_1$-antitrypsin plasmid) was concentrated 7.5-fold by UF, and diafiltered against 10 diavolumes of Milli-Q water.

Analysis of the final product, $\alpha_1$-antitrypsin plasmid, indicated the preparation 95% plasmid DNA, <5% RNA, 0.05% E. coli DNA, <0.06% protein, <0.2 Eu//mg of plasmid DNA for endotoxins, and complete removal of denatured plasmid DNA. This represents a reduction by the HIC resin in bacterial chromosomal DNA of between 10 and 100-fold from what typically contaminates plasmid preps after the DEAE anion chromatography step. In addition, RNA was reduced between 1 and 2-fold, endotoxin levels were lowered at least 250-fold, both protein and denatured plasmid levels have been reduced to essentially zero.

It should also be pointed out that most HIC resins will bind supercoiled DNA at $\geq$2M $(NH_4)_2SO_4$ while the open circle form will not bind under these conditions. This allows for a significant enrichment of the supercoiled plasmid DNA in the final product. Thus HIC resins in conjunction with anionic-exchange resins offer the ability at large-scale to remove a substantial amount of contaminants which copurify with the plasmid DNA on ion-exchange resins. In addition, HIC resins can be used to selectively purify supercoiled plasmid DNA.

Example 9

A Hydrolysis Assay

This assay is used to quantify the amount of RNA present in a solution of plasmid DNA.
Standard Curve
(1) Use E. coli rRNA as standards from Sigma; ribonucleic acid, ribosomal from E. coli, Strain W; Cat. No. R-7628). Make up rRNA to concentrations of 0, 10, 20, 30, 40 and 50 µgs/ml by diluting the resuspended RNA in water.
(2) Run 367 µl of each standard through RNA hydrolysis procedure (see below).
(3) Plot standards with concentration versus A260 and curve fit with a linear fit, forcing the curve through zero.
(4) Use the slope from the curve to calculate sample RNA concentrations.
Hydrolysis Procedure
(1) Take 467 µls of sample. If necessary, dilute before taking 467 µls so that RNA is less than 50 µgs/ml. Put samples in screw cap tubes so that tubes do not pop open during heating.
(2) Add 33 µl 1.5M KOH to bring volume to 0.5 mls.
(3) Heat at 110° C. for 1 hour. The heat and alkali will hydrolyze the RNA.
(4) Turn off heat block after one hour, leaving the samples in the block, and allow samples to cool to less than 100° C. (about 10 minutes).
(5) Remove from heat block and add 32 µls of 10% HCl.
(6) Add 968 µls 100% ethanol to bring volume to 1.5 mls. The absolute ethanol will precipitate the DNA in the sample.
(7) Place the samples at −20° C. for at least 20 minutes.
(8) Centrifuge samples at 4° C. for at least 15 minutes at 14,000 rpm.
(9) Blank UV spectrophotometer with WFI, water for injection or MilliQ water. Measure A260 and A232 of supernatants.
(10) Use A260 to calculate RNA concentration with the standard curve and, if necessary, use A232 to adjust for protein.

One skilled in the art would readily appreciate that the present invention is well adapted to carry out the objects and obtain the ends and advantages mentioned, as well as those inherent therein. The methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

What is claimed is:

1. A method for purifying plasmid DNA from a plasmid pool comprising contacting the plasmid pool with a hydrophobic interaction chromatography (HIC) resin in an aqueous medium, and eluting the plasmid DNA from one or more contaminants in the plasmid pool solution with a non-volatile, non-flammable elution solution.

2. The method of claim 1, wherein the HIC resin is moderately hydrophobic and comprises alkyl chain ligands.

3. The method of claim 2, wherein the alkyl chain ligands are selected from the group consisting of octyl, phenyl, and butyl alkyl chain ligands.

4. The method of claim 1, wherein the resin comprises agarose.

5. The method of claim 4, wherein the HIC resin comprising agarose is selected from the group consisting of octyl sepharose, phenyl sepharose, and butyl sepharose.

6. The method of claim 1, wherein the HIC resin is selected from the group consisting of octyl sepharose, phenyl sepharose, butyl sepharose and phenyl 650-S.

7. The process of claim 1, wherein the aqueous solution comprises a salt at a concentration of at least 1.6 molar.

8. The method of claim 1, wherein said aqueous medium contains a multivalent salt selected from the group consisting of ammonium salts, sodium salts, potassium salts, and combinations thereof.

9. The method of claim 8, wherein the multivalent salt is selected from the group consisting of ammonium sulfate, sodium citrate and potassium phosphate salts.

10. A process for isolating a plasmid DNA from E. coli bacterial cells, comprising the steps of:
(1) fragmenting and harvesting the cells;
(2) exposing the cells to alkaline lysis and precipitation thereby forming a plasmid pool containing plasmid DNA and one or more contaminants;
(3) purifying the plasmid pool by hydrophobic interaction chromatography (HIC) in an aqueous solution containing a salt at concentration of at least 1.6 M; and
(4) eluting the plasmid DNA from one or more contaminants of the plasmid pool with a non-volatile, non-flammable elution solution, thereby forming a HIC-purified plasmid DNA.

11. The process of claim 10, wherein the HIC is performed using a HIC resin that is moderately hydrophobic due to alkyl chains as ligands.

12. The process of claim 11, wherein the alkyl chain ligands are selected from the group consisting of: octyl, phenyl, and butyl alkyl chain ligands.

13. The method of claim 11, wherein the HIC is performed at a salt concentration wherein the plasmid DNA is collected in a flow through fraction and residual RNA, endotoxin, and *E. coli* DNA from the plasmid pool remain bound to the resin.

14. The method of claim 11, wherein the HIC is performed at a salt concentration wherein a supercoiled plasmid DNA population is bound to resin and a relaxed and/or nicked circular plasmid population is allowed to flow through the resin.

15. The process of claim 10, wherein the salt is selected from the group consisting of ammonium, sodium, and potassium salts, and combinations thereof.

16. The method of claim 10, where the plasmid DNA is not precipitated, exposed to elevated temperatures or acidic pH, and wherein the method uses no organic solvents.

17. A method of separating supercoiled plasmid DNA from a mixture of supercoiled plasmid DNA and relaxed open circle plasmid DNA and optionally, at least one host cell impurity, comprising the following steps:

(a) forming a solution by adding a salt at high concentration to the mixture of supercoiled plasmid DNA and relaxed plasmid DNA and, when present, said at least one host cell impurity;

(b) contacting the solution with a chromatography support comprising a hydrophobic ligand at a salt concentration where the supercoiled plasmid DNA and the relaxed plasmid DNA differentially interact with the hydrophobic ligand leading to a resolutions of forms; and (c) altering the salt concentration to a low salt concentration to remove supercoiled plasmid DNA from the chromatography support under conditions using a non-volatile, non-flammable elution solution where, when present, said at least one host cell impurity is retained on the support.

18. The method of claim 17, wherein the impurity is selected from the group consisting of chromosomal DNA, RNA, protein, endotoxin, and combinations thereof.

19. The method of claim 17, wherein said hydrophobic ligand is an alkyl chain ligand selected from the group consisting of octyl, phenyl, and butyl alkyl chain ligands.

20. The process of claim 17, wherein the salt at high concentration is at least 1.6 molar.

* * * * *